United States Patent [19]

Dirksing et al.

[11] Patent Number: 5,006,004
[45] Date of Patent: Apr. 9, 1991

[54] TOPICAL APPLICATOR FOR LIQUID

[75] Inventors: Robert S. Dirksing; Theodore F. Merz, both of Cincinnati, Ohio

[73] Assignee: The Proctor & Gamble Company, Cincinnati, Ohio

[21] Appl. No.: 125,291

[22] Filed: Nov. 25, 1987

[51] Int. Cl.$^5$ .................... A47L 13/30; B43K 5/00; B43M 11/06
[52] U.S. Cl. .................... 401/261; 401/262; 401/265; 604/310
[58] Field of Search ............... 401/199, 284, 261, 265, 401/292, 22, 23, 25, 28, 266, 183; 604/258, 289, 310

[56] References Cited

U.S. PATENT DOCUMENTS

| | | | |
|---|---|---|---|
| Re. 14,115 | 4/1916 | Winkelmiller et al. | |
| 566,558 | 8/1896 | Bell | 401/284 |
| 753,968 | 3/1904 | Farmer | 604/310 X |
| 817,890 | 4/1906 | Williams | |
| 945,982 | 1/1910 | Pomphrey | |
| 1,137,086 | 4/1915 | Rodiger | |
| 1,340,926 | 5/1920 | Weitz | 401/258 |
| 1,560,061 | 11/1975 | Kish | 401/183 |
| 1,772,608 | 8/1930 | Kristofek | 401/183 |
| 1,824,275 | 9/1931 | Kellogg, Jr. | 401/258 |
| 2,289,998 | 7/1942 | Salz | 401/258 |
| 2,517,027 | 8/1950 | Rado | 222/94 |
| 2,849,009 | 8/1958 | Heinrich et al. | |
| 2,896,237 | 7/1959 | Owens et al. | 15/136 |
| 2,913,747 | 11/1959 | Hempel | 15/136 |
| 3,015,836 | 1/1962 | Maynier et al. | |
| 3,016,173 | 1/1962 | Stull | 222/541 |
| 3,247,828 | 4/1966 | Basham | 401/199 X |
| 3,271,810 | 9/1966 | Raffe | 15/539 |
| 3,454,196 | 7/1969 | Hazard | 222/83 |
| 3,481,675 | 12/1969 | Greenberg | 401/183 |
| 3,777,949 | 12/1973 | Chiquiari-Arias | 222/541 |
| 3,949,871 | 4/1976 | Christensen et al. | 206/229 |
| 3,961,635 | 6/1976 | Miya | |
| 3,994,412 | 11/1976 | Difiglio | 220/266 |
| 4,002,182 | 1/1977 | Michel | 132/88.7 |
| 4,139,619 | 2/1979 | Chidney | 424/45 |
| 4,218,155 | 8/1980 | Weidner | 401/132 |
| 4,358,028 | 11/1982 | Chiquiar-Arias | 222/107 |
| 4,408,699 | 10/1983 | Stock | 222/149 |
| 4,413,753 | 11/1983 | Stock | 222/149 |
| 4,572,689 | 2/1986 | Chernack | 401/132 |
| 4,596,812 | 6/1986 | Chidney et al. | 514/256 |
| 4,602,650 | 7/1986 | Pipkin | 132/84 R |
| 4,636,203 | 1/1967 | Emanis et al. | 604/310 |
| 4,738,669 | 4/1988 | Vlock | 604/289 |

FOREIGN PATENT DOCUMENTS

| | | | |
|---|---|---|---|
| 0210051 | 1/1987 | European Pat. Off. | 401/284 |
| 1065144 | 9/1959 | Fed. Rep. of Germany | |
| 2558069 | 6/1977 | Fed. Rep. of Germany | 401/199 |
| 122792 | 11/1960 | New Zealand | |
| 130616 | 2/1964 | New Zealand | |
| 2173743 | 10/1986 | United Kingdom | |

Primary Examiner—Richard J. Apley
Assistant Examiner—D. F. Crosby
Attorney, Agent, or Firm—E. Kelly Linman; John V. Gorman; Richard C. Witte

[57] ABSTRACT

A dispenser for the topical application of a liquid product. In a preferred embodiment of the present invention, the dispenser comprises a compressible reservoir, a feed tube, a smooth, substantially non-porous applicator tip, and a tip cover. Compression of the reservoir causes liquid product to flow onto the exposed surface of the applicator tip and form an encapsulating sheet of the liquid product. The liquid product may then be transferred from the applicator tip to the surface to be treated by contacting the surface with the liquid product coated applicator tip.

4 Claims, 3 Drawing Sheets

TOPICAL APPLICATOR FOR LIQUID

BACKGROUND OF THE INVENTION

Topical drugs, particularly those employed for the purpose of restoring hair growth, are most effective when delivered to the scalp and, even more importantly, to the hair follicles. In circumstances where the scalp is hairless, direct application of such drugs over a broad surface can be achieved by a multitude of simple means such as painting or wiping. Many applicators have been developed which would satisfy this requirement. For example, U.S. Pat. No. 4,572,689 issued to Chernack on Feb. 25, 1986 discloses a disposable applicator which employs a bristle brush to paint a liquid product onto a surface. Other applicators which use porous materials for applying liquids have also been disclosed. disclosed. U.S. Pat. Nos. 2,913,747 issued to Hempel on Nov. 24, 1959; 3,271,810 issued to Raffe on Sept. 13, 1966; and 4,218,155 issued to Weidner on Aug. 19, 1980 employ felt, rubber or plastic sponge, and open cell plastic foam, respectively, as the applicator surfaces.

However, assuming the drug is effective and that the subject using the drug is only partially bald, a means to efficiently apply the drug to the scalp rather than existing hair is highly desirable. The presence of hair requires the drug be delivered down through the hair and around the hair shafts. This condition may be satisfied by a dispenser which presents the dispensed liquid from a small opening at the tip of an extension from the body of the container or reservoir. Such dispensers are disclosed in U.S. Pat. Nos. 2,896,237 issued to Owens on July 28, 1959 and 3,777,949 issued to Chiquiari-Arias on Dec. 11, 1973.

In reality, varying degrees of baldness will be present with different subjects at the commencement of the treatment. Also, as the treatment progresses, each particular subject will be required to treat the scalp with varying degrees of hair present.

The application of a hair restoration drug is basically a "blind" operation in that the subject may often not be able to see the actual application of the drug, i.e., at the back of the head or under the hair. The application will be accomplished primarily by feel, whether by the actual contact of the applicator or by the cooling effect of the liquid applied. Therefore, a quick feedback between the act of compressing the reservoir and the presence of liquid on the scalp is very important. Porous applicator surfaces delay the feedback by requiring the applicator to become saturated. Additionally, some rigid porous applicators will retain a quantity of the liquid which is essentially unavailable for dispensing.

As the human scalp is sensitive, the applicator surface should be smooth and low friction. It should also have no jagged projections such as may be left at the break away tips of dispensers such as disclosed in U.S. Pat. No. 3,777,949 issued to Chiquiari-Arias on Dec. 11, 1973.

Further, the applicator should resist soiling by hair and scalp.

In light of the above, a principal object of the present invention is to provide a simple dispenser for the application of a liquid product, e.g., a hair restoring drug, which will enable the user to accurately and comfortably apply the liquid product to both broad surfaces or specific points.

Another object of the present invention is to provide an inexpensive disposable dispenser which is fully sealed until the time of use.

A further object of the present invention is to provide a dispenser which permits the user to effectively treat the scalp in the presence of hair with minimal disruption of the hair style as well as quickly treat broad areas of the scalp where little or no hair is present.

DISCLOSURE OF THE INVENTION

In a particularly preferred embodiment, the present invention comprises a dispenser for the topical application of a liquid product, such as a hair restoring drug, to a surface such as the human scalp. The dispenser comprises a compressible reservoir in fluid communication with a smooth, substantially non-porous applicator tip. In use, the applicator tip has an exposed portion and a non-exposed portion. The applicator tip preferably comprises a cylinder with a round exposed end. The applicator tip also employs a multiplicity of grooves oriented substantially parallel to the axis of the tip. The grooves, which extend from the non-exposed to the exposed portion of the applicator tip, are in fluid communication with the compressible reservoir. Compression of the reservoir causes the liquid product contained therein to flow onto the exposed surface of the applicator tip via the aforementioned grooves. The substantially non-porous applicator tip maerial and surface finish are selected so that the solvent used in the liquid product will wet the surface of the applicator tip with a sheeting action when placed in contact therewith. The liquid product sheeted onto the surface of the applicator tip may then be transferred to discrete points of end use using the rounded tip of the applicator or broadly applied to an entire surface by orienting the sides of the applicator tip substantially tangential to the surface to be treated.

Dispensers of the present invention may be of the single use or refillable variety. The units may be delivered to the end user in a completely sealed configuration including a tip cover integrally molded with the dispenser shell or with refastenable tip cover and/or reservoir closure means.

BRIEF DESCRIPTION OF THE DRAWINGS

While the specification concludes with claims that particularly point out and distinctly claim the subject matter regarded as forming the present invention, it is believed that the invention will be better understood from the following description and drawings in which:

DETAILED DESCRIPTION OF THE INVENTION

Figure 1:
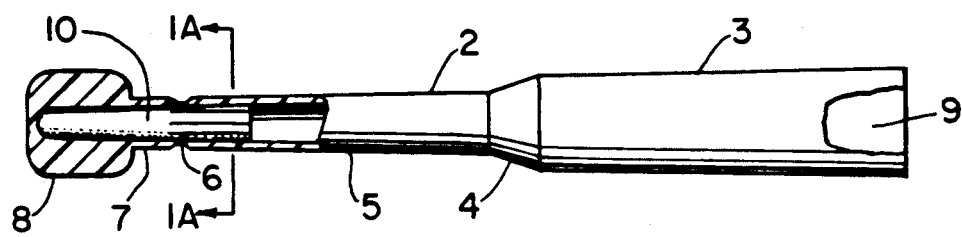
FIG. 1 is a partial cross-sectional illustration of a preferred dispenser with its applicator tip shown in the assembled position, said dispenser being shown prior to filling and sealing.

In FIG. 1 there is shown a particularly preferred dispenser embodiment of the present invention comprising topical applicator 1. Topical applicator 1 comprises an applicator shell 2 and a smooth surfaced applicator tip 10. Applicator shell 2 is preferably comprised of a compressible reservoir portion 3 which merges into a conical portion 4 which further merges into a barrel portion 5, a weakened portion 6 and a tip cover portion 7 including a twist tab 8. Inserted within the barrel portion 5 and extending beyond weakened portion 6 into tip cover portion 7 is the solid applicator tip 10. The bore of barrel portion 5 is preferably somewhat smaller than the largest diameter of applicator tip 10 so that the applicator tip 10 can be securely held within the bore of barrel 5 by a slight degree of interference. The interior walls of reservoir portion 3, conical portion 4, and barrel portion 5 along with the interior surface 15 of applicator tip 10 generally define liquid product chamber 9.

Applicator shell 2 may be manufactured in one piece by molding processes such as blow molding or injection molding of various plastic materials such as polyethylene or polypropylene.

Figure 1A:
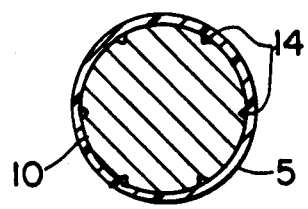
FIG. 1A is a cross-sectional view of the dispenser shown in FIG. 1, taken along section line 1A—1A of FIG. 1.
Figure 2:
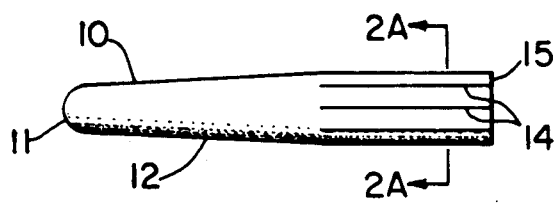
FIG. 2 is an enlarged view of the solid applicator tip used in the dispenser embodiment shown in FIG. 1.

FIG. 2 is an enlarged view of applicator tip 10, which preferably comprises a cylinder including a rounded end portion 11, a generally tapered portion 12 and a straight portion 13 of substantially constant diameter along its length. At least one, and preferably a multiplicity of metering grooves 14 are provided at least along the straight portion 13 of the applicator tip. The metering grooves 14 and the interior wall of the barrel portion 5 of shell 2 form discrete passageways for transferring liquid product to the exposed portion of the applicator tip 10 whenever the reservoir 3 is compressed. The metering grooves 14 and their relationship to the barrel portion 5 of shell 2 are best shown in the cross-sections of FIGS. 2A and 1A, respectively. To enhance the user's ability to control the flow of liquid product 80 onto the applicator tip 10, the cross-sectional flow area provided by each metering groove 14 should preferably be sufficiently small that liquid product 80 contained within product chamber 9 will not be discharged through the metering groove unless the compressible reservoir 3 is subjected to squeezing.

Figure 2B:
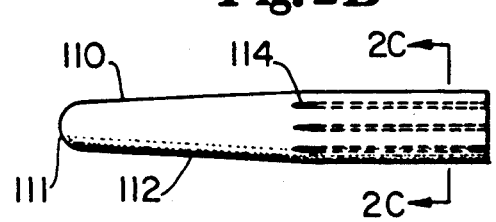
FIG. 2B is an enlarged view of an alternative solid applicator tip which could be used with the dispenser shell shown in FIG. 1.
Figure 2A:
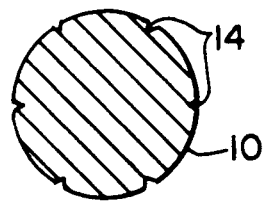
FIG. 2A is a cross-sectional view of the applicator tip shown in FIG. 2, taken along section line 2A—2A of FIG. 2.
Figure 2C:
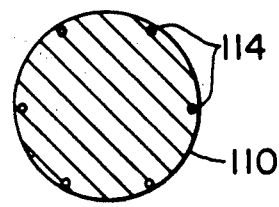
FIG. 2C is a cross-sectional view of the applicator tip shown in FIG. 2B, taken along section line 2C—2C of FIG. 2.

An alternative applicator tip 110 employing a multiplicity of internal passageways 114 is shown in FIGS. 2B and 2C. Like the metering grooves 14, the passageways 114 extend from the non-exposed to the exposed portions of the applicator tip 110. Liquid product 80 is distributed about the periphery of the exposed surface of the applicator tip 110 through the passageways 114 and thereafter sheets onto the tapered portion 112 and the rounded end portion 111 of the applicator tip 110 in a manner identical to tip embodiment 10 shown in FIG. 2.

Figure 2D:
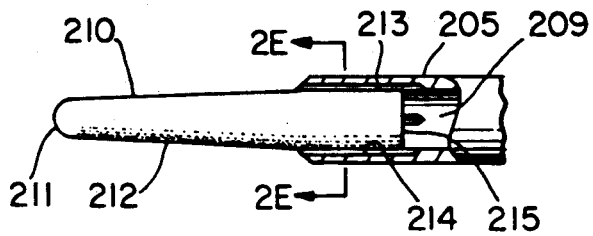
FIG. 2D is an enlarged view of an alternative solid applicator shown within a partial cross-section of an alternative dispenser embodiment.
Figure 2F:
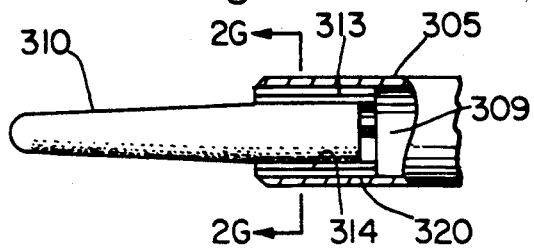
FIG. 2F is an enlarged view of an alternative solid applicator shown within a partial cross-section of an alternative dispenser embodiment which includes a flow bushing.
Figure 2E:
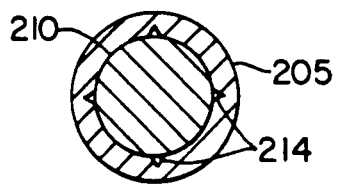
FIG. 2E is a cross-sectional view of the applicator tip and dispenser shown in FIG. 2D, taken along section line 2E—2E of FIG. 2D.

Another alternative applicator tip 210 with uninterrupted cylindrical surface 213 is shown in FIGS. 2D and 2E. Unlike the metering grooves 14 which are formed into the cylindrical surface 13, the metering grooves 214 are formed in the interior surface of barrel portion 205. Metering grooves 214 extend beyond interior surface 215 of applicator tip 210 into the product chamber 209. Liquid product 80 is distributed about the periphery of the exterior surface of the applicator tip 210 through the metering grooves 214 and thereafter onto the tapered portion 212 and the rounded end portion 211 of the applicator tip 210 in a manner similar to the embodiment 10 shown in FIG. 2.

Figure 2G:
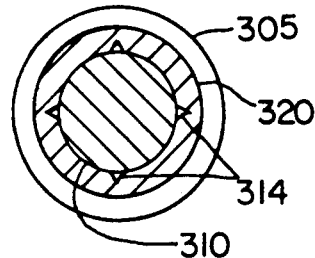
FIG. 2G is a cross-sectional view of the applicator tip, feed bushing and dispenser shown in FIG. 2F, taken along section line 2G—2G of FIG. 2F.

Still another alternative applicator tip 310 which is used in conjunction with liquid passage bushing 320 is shown in FIGS. 2F and 2G. Liquid passage bushing 320 includes metering grooves 314 which provide a similar function as described for metering grooves 214. Liquid passage bushing 320 is positioned intermediate the interior wall of barrel portion 305 and applicator tip 310. If desired, the grooves 314 could be eliminated from liquid passage bushing 320 and the bushing could be constructed of a porous rather than a non-porous material. In the latter embodiment, the porous bushing would be used for transferring liquid product from the product chamber 309 to the exposed portion of the applicator tip 310. In the latter embodiment, the entire porous bushing functions as the liquid passageway.

Figure 2J:
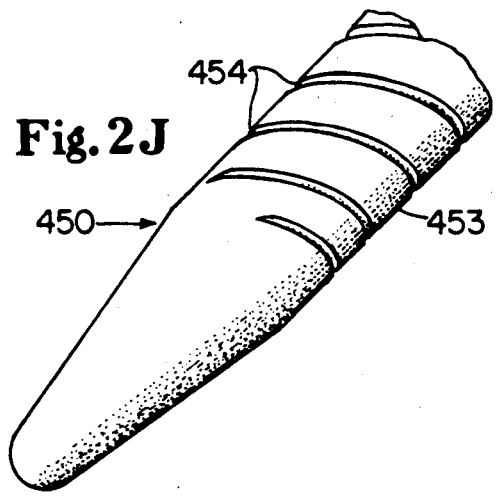
FIG. 2J is a perspective view of an alternative applicator tip having spiral feed grooves which could be used with the dispenser shell shown in FIG. 1.
Figure 2I:
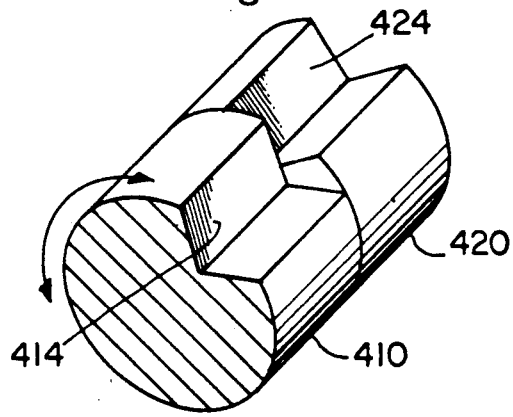
FIG. 2I is a perspective view of a portion the adjustable applicator tip of FIG. 2H showing a partial misalignment of one of the metering passageways.
Figure 2H:
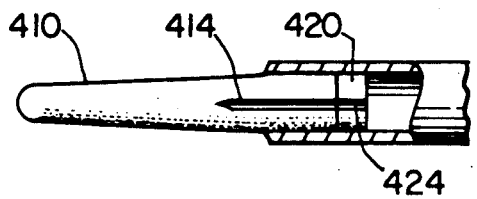
FIG. 2H is an enlarged view of an alternative applicator tip including means for adjusting flow rate shown within a partial cross-section of a dispenser shell of the type generally disclosed in FIG. 1.

Still another alternative applicator tip 410 with throttling insert 420 is shown in FIGS. 2H and 2I. Applicator tip 410 may be positioned or rotated relative to throttling insert 420 to variably restrict the passageway or passageways from the product chamber 9 to the exposed surface of applicator tip 410. In the illustrated embodiment, only a single passageway has been shown. Metering groove 424 of throttling insert 420 is shown with some angular misalignment relative to the metering groove 414 of applicator tip 410. The result is an orifice of reduced cross-section relative to either metering groove 414 or metering groove 424. The purpose of this embodiment is to provide variable control of the rate at which product 80 will be expelled from product chamber 9 when the compressible reservoir 3 is squeezed. If desired, the position of the throttling insert 420 may be fixed relative to the barrel portion 5 of the shell and a predetermined calibration may be applied to the applicator tip 410 and the barrel portion 5 of the shell to permit the liquid product application rate to be optimized to the condition of the surface to be treated by rotating the applicator tip 410.

It is not a prerequisite of the present invention that the liquid passageway(s) be straight or that they be oriented substantially parallel to the longitudinal axis of the applicator tip. For example, an alternative applicator tip 450 with spiral metering grooves 454 formed into cylindrical surface 453 is shown in FIG. 2J. The choking effect provided by the metering grooves is increased for a given cross-section by increasing the length of the path that the liquid product 80 is caused to travel. The spiral grooves provide such an increased path length. Nearly any path can be employed, so long as the non-exposed end of the applicator tip, which is secured in fluid communication with the compressible reservoir, is placed in fluid communication with the exposed portion of the applicator tip by the liquid passageway(s) thus formed. Of course, the spiral grooves could be substituted for metering grooves 214 in FIGS. 2D and 2E, for metering grooves 314 in liquid passage bushing 320 in FIGS. 2F and 2G, or for metering grooves 424 and 414 in throttling insert 420 and applicator tip 410, respectively, shown in FIGS. 2H and 2I.

Figure 4:
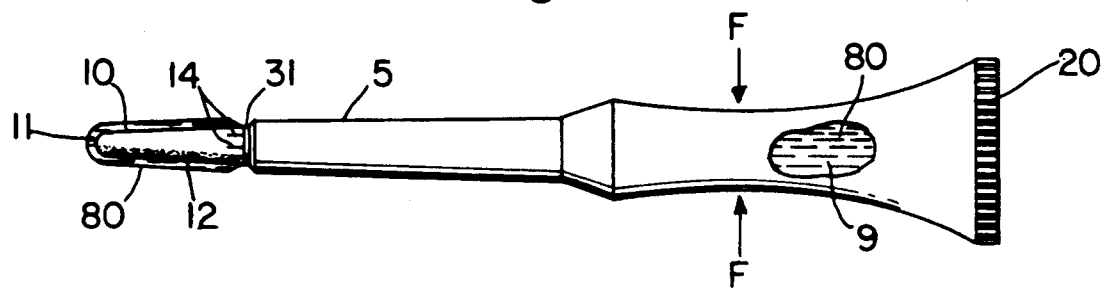
FIG. 4 is an illustration of the dispenser shown in FIG. 3 with the twist-off cover removed and the applicator tip exposed, said dispenser being subject to opposing squeezing forces "F"

Referring again to FIG. 1, the surface of applicator tip 10 is preferably substantially non-porous and may be produced from various materials by processes such as injection molding, compression molding, or casting. For maximum effectiveness in dispensing, the liquid product 80 to be dispensed by squeezing the compressible reservoir 3 preferably wets the exposed surface of the applicator tip 10 so that said liquid product spreads onto and effectively coats the surface of said applicator tip, as generally shown in FIG. 4.

The choice of the particular material and texture of the surface of applicator tip 10 relative to the wetting properties of the liquid product 80 is important to the performance of the topical applicator. The surface of applicator tip 10 should be wettable by liquid product 80, i.e., liquid product 80 should spread out over and intimately contact the surface of applicator tip 10. If desired, wetting agents which increase the spreading of a liquid onto a particular surface may be added to the liquid product 80.

The concept of wettability may be better understood from the following examples. If rain water falls upon a well weathered surface of an automobile hood, the rain tends to spread out and evenly cover the hood surface. In this case, the car hood is said to be wettable by the rain water. If the same car hood were to be waxed, rain water would tend to bead up on the freshly waxed surface. In this example, the surface of the car hood would be considered non-wettable by the rain water. However, if a quantity of detergent (wetting agent) is added to a bucket of the same rain water and this solution is then applied to the waxed hood surface of the car, the water/detergent solution will again spread out evenly across the car surface. In other words, the car hood is wettable by the water/detergent solution.

When the liquid product 80 comprises a liquid form of a hair restoration drug of the type generally disclosed in U.S. Pat. No. 4,139,619 issued to Chidsey, III on Feb. 13, 1979 and/or U.S. Pat. No. 4,596,812 issued to Chidsey, III et al. on Jan. 24, 1986, which patents are hereby incorporated herein by reference, an applicator tip 10 comprised of molded polypropylene and exhibiting a substantially smooth exposed surface will usually produce satisfactory sheeting action.

Figure 1B:
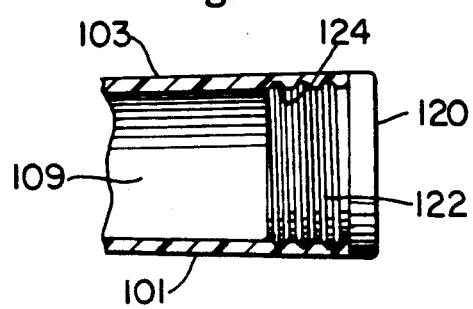
FIG. 1B is a partial cross-sectional segment of an alternative dispenser embodiment of the present invention.
Figure 3:
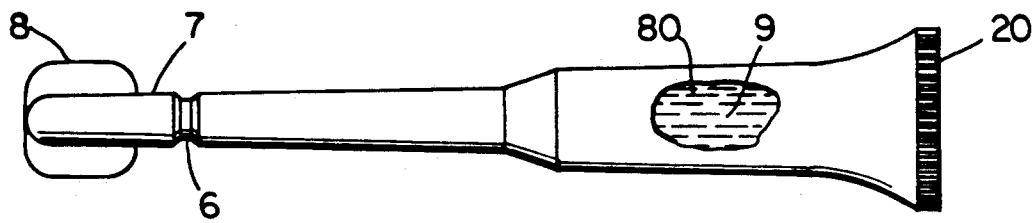
FIG. 3 is an illustration of the dispenser shown in FIG. 1 after filling and sealing.

FIG. 3 is a view of a filled topical applicator 1 including an end seal 20. End seal 20 may be produced by conventional sealing means such as an ultrasonic welding apparatus or an impulse heat strip. If the topical applicator is intended to be reused, a removable end closure, such as a threaded cap, could of course be provided in lieu of end seal 20. Such a topical applicator embodiment 101 is shown in the segment of FIG. 1B, wherein a cap 120 includes a threaded portion 122 which mates with internal threads 124 provided in the reservoir portion 103 of the shell to form a product chamber 109. The balance of the topical applicator 101 may be identical to topical applicator 1 shown in FIG. 1.

The filled and sealed topical applicator 1 shown in FIG. 3 is generally in the form it would be delivered to the user of the device. Weakened section 6 in shell 2 preferably comprises a reduction in the thickness of the wall in shell 2.

To prepare the topical applicator 1 for use, the user preferably grasps the twist tab 8 on tip cover portion 7 in one hand and the general exterior surface of the applicator shell 2 opposite weakened portion 6 in the other hand and twists in opposite rotations. This causes a fracture 31 within weakened portion 6 and permits tip cover portion 7 and the integral twist tab 8 to be removed. This of course exposes a substantial portion of applicator tip 10, as generally shown in FIG. 4. The non-exposed portion of the applicator tip 10, i.e., the portion remaining within barrel portion 5, is also defined by fracture 31. The fracture 31 intersects the metering grooves 14 so that the liquid product 80 squeezed from the confines of product chamber 9 may begin a sheeting action onto the exposed portion of the applicator tip 10 as soon as it passes the fracture 31.

FIG. 4 is a view of a topical applicator 1 in a condition ready to apply the liquid product 80 to the target surface, e.g., a hair restoring drug to the scalp. To achieve the condition shown in FIG. 4, the user preferably grasps the compressible reservoir portion 3 between the fingers and applies opposing squeezing forces "F" which compress the compressible reservoir portion 3 of the product chamber 9, thereby causing liquid product 80 to flow through the discrete passageways defined by metering grooves 14 and the interior surface of barrel portion 5. The liquid product 80 emerges from metering grooves 14 onto the exposed surface of applicator tip 10 at the point of fracture 31. The liquid product 80 then sheets out onto the entire surface of the generally tapered or conical portion 12 and rounded portion 11 of applicator tip 10, as generally shown in FIG. 4. If additional liquid product 80 is squeezed from the reservoir onto the surface of applicator tip 10, beyond the amount that would form a generally even film, welling of said liquid product 80 at the lowermost location on said applicator tip 10 will occur due to gravity. This phenomenon may be described as supersaturation of the applicator tip. In the extreme, liquid product 80 can be caused to drip from the surface of applicator tip 10. This could be the case if either: (a) liquid product 80 is delivered to the surface of applicator tip 10 at a rate faster than the transfer rate to the surface to be treated; or (b) the applicator tip 10 is not in contact with a treatment surface. Once the excess liquid product 80 drips from the surface of applicator tip 10, the liquid product 80 remaining on the applicator tip 10 will generally recover to a substantially even coating as generally illustrated in FIG. 4.

When used in the context of hair restoration, the liquid product 80 that coats the applicator tip 10 can be comprised of any suitable drug. Liquid forms of particularly preferred hair restoration drugs are disclosed in the aforementioned U.S. Pat. No. 4,139,619 issued to Chidsey, III and the aforementioned U.S. Pat. No. 4,596,812 issued to Chidsey, III et al., which patents are incorporated herein by reference. The drug compositions disclosed in the aforementioned patents contain as one of their active ingredients 6-amino-1,2-dihydro-1-hydroxy-2-imino-4-piperodinopyrimidine, hereinafter referred to by the coined term "MINOXIDI" ®. If necessary, the amount of solvent present in the particular drug selected can be adjusted to provide the desired liquid sheeting behavior when the drug comprising liquid product 80 is delivered to the surface of the applicator tip 10.

The liquid product 80 that coats the applicator tip 10 is transferred to the surface of the scalp as the user paints the area to be treated. If the treatment area is relatively large and free of hair, rapid coverage of the scalp with the hair restoring drug 80 can be accomplished by positioning the generally tapered or conical portion 12 so that its surface is substantially tangent to the scalp and stroking the topical applicator 1 along a path generally perpendicular to the axis of the applicator tip. Supersaturation of applicator tip 10 as described above can be employed to the user's advantage to quicken the drug application process. The heavy loading of the liquid product 80 at the lowermost location on the applicator tip 10 will most likely be at the point or line in contact with the surface to be treated. If the hair restoring drug 80 is to be applied to a smaller or more specific area, such as at the base of the hair shafts (as might be the situation with existing but possibly thinning hair), the rounded portion 11 may be used as the applicator. Use of the rounded portion 11 in this manner minimizes the transfer of the hair restoring drug 80 to the hair, where it would be of little value to the user.

The added length provided by barrel portion 5 facilitates application of a hair restoring drug 80 at the base of the hair shafts even in situations where the user employs a lofty hair style. During this process, the user simply a squeezes the compressible reservoir portion 3 to control the degree of wetness on the exposed portions of applicator tip 10. The partial vacuum that develops within product chamber 9 upon removal of opposing squeezing forces "F" is relieved by the passage of air through the passageways formed by metering grooves 14 and the inner wall of barrel portion 5. The user continues to pulse the compressible reservoir portion 3 with opposing squeezing forces "F" until the liquid product contents of the applicator are exhausted or until the desired amount of drug application has been accomplished.

Because the applicator tip 10 is generally smooth and rigid, it easily glides across the surface of the scalp with little tendency to become entangled with the hair. The user can employ a combination of sensory perceptions to control the application of the hair restoring drug 80. Visual control may not be practical because of obscured view due to the location of the scalp surface to be treated, e.g., behind the head, or due to the presence of hair over the scalp surface to be treated. More likely, the user will use a combination of physical contact and cooling sensations to control the position of the applicator and the amount of drug applied. Because the applicator tip 10 is substantially non-porous, it has no inherent reservoir. Consequently, compression of the compressible reservoir portion 3 by opposing forces "F" results in an almost immediate presentation of liquid product 80 on the exposed portion of the applicator tip 10. This further enhances the uniformity of the application process by providing the user with better and quicker feedback.

Furthermore, because of the solid non-porous nature of the applicator tip 10, the problem of contamination of the applicator tip with scalp and hair soil along with the accompanying bacterial load is substantially reduced in comparison to porous or bristle type applicators used in prior art dispensers.

If the contents of topical applicator 1 are not completely exhausted in a single use, the tip cover portion 7 may be reinserted over the applicator tip 10 for storage and future use.

Figure 5:
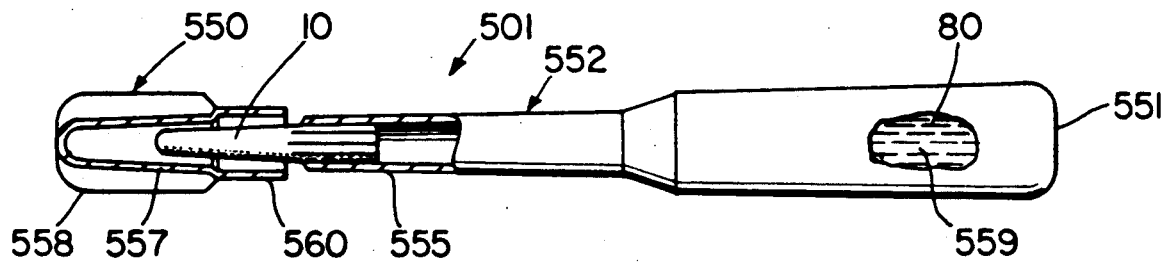
FIG. 5 is a partial cross-sectional illustration of an alternative embodiment of a dispenser of the present invention shown with its tip cover in a partially assembled position.

FIG. 5 illustrates another embodiment 501 of a generally similar topical applicator of the present invention in a partially assembled condition. In topical applicator 501 the end seal 20 of the embodiment 1 shown in FIG. 3 is replaced by an integral end wall portion 551. Integral end wall portion 551 may be provided by plastic processing means such as extrusion blow molding. Applicator tip 10 may be installed into applicator shell 552 after reservoir 559 has been charged with liquid product 80.

Applicator tip cover 550 shown in FIG. 5 comprises of tip cover portion 557, a gripping tab 558, and a collar 560. When fully assembled, collar 560 fits snugly about or snaps onto the terminal end of barrel portion 555 of shell 552 to generally seal the applicator contents and cover the exposed portion of the applicator tip 10. The interior of tip cover portion 557 preferably closely envelops the external surface of applicator tip 10 to minimize the amount of liquid product 80 which can migrate from product chamber 559 prior to removal of the tip cover 550. Applicator tip cover 550 may also be used to facilitate the assembly of applicator tip 10 into the terminal end of barrel portion 555 by supporting the applicator tip during assembly. Gripping tab 558 is preferably used to facilitate removal and replacement of the applicator tip cover 550.

Although the description of the topical applicator of the present invention has been in the context of a hair restoring scalp treatment, said topical dispenser is particularly well suited for many other uses, particularly medicinal uses, e.g., antiseptic treatment of wounds or burns and fungicidal treatment of athlete's food. In the case of the latter, the applicator tip would easily fit between toes and, because its surface is non-porous, fungus spores and bacteria would not be readily retained or transferred to non-infected areas.

Additionally, the topical applicator may be used in non-medical applications, such as a dispenser for a spot remover or a pretreatment applicator for stains in clothing.

While particular embodiments of the present invention have been illustrated and described, it will be obvious to those skilled in the art that various changes and modifications can be made without departing from the spirit and scope of the present invention, and it is intended to cover in the appended claims all such modifications that are within the scope of this invention.

What is claimed is:

1. A dispenser for the substantially uniform topical application of a liquid product either to discrete isolated portions of the surface of an object or to the entire surface of said object, said dispenser comprising:
   (a) a compressible reservoir for housing said liquid product;
   (b) an applicator tip comprised of substantially non-porous material and having a longitudinal axis and an external surface comprising an exposed portion and a non-exposed portion, said exposed and non-exposed portions being located adjacent one another along said longitudinal axis, said non-exposed portion of said applicator tip being secured in fluid communication with said compressible reservoir, said non-exposed portion of said applicator tip also being in fluid communication with the exposed portion of said applicator tip by means of at least one liquid passageway at least partially comprising said applicator tip, said liquid passageway extending from said compressible reservoir to the initial point of exposure of said exposed portion of said applicator tip, said liquid passageway having a cross-section which is sufficiently small that it will resist the flow of liquid from said compressible reservoir when said liquid is acted upon solely by gravitational forces, whereby liquid product can be transferred from said compressible reservoir to said exposed surface of said applicator tip along said liquid passageway when said reservoir is compressed, said exposed portion of said applicator tip extending beyond said at least one liquid passageway comprising a cylinder having a rounded end, said cylinder and said rounded end exhibiting a substantially non-porous surface which is sufficiently smooth that said liquid product will sheet substantially uniformly onto said smooth surfaced cylinder and rounded end of said applicator tip as soon as said liquid product exits said at least one liquid passageway, whereby said uniformly sheeted liquid product on said exposed portion of said applicator tip can thereafter be transferred either to discrete isolated portions of the surface of an object by contacting said discrete isolated portions with said liquid product coated rounded end portion of said applicator tip or to the entire surface of said object by tangentially stroking said entire surface with the periphery of said liquid product coated cylinder portion of said applicator tip in a direction substantially perpendicular to the axis of said cylinder; and
   (c) an applicator tip cover for totally enclosing the exposed portion of said applicator tip prior to placing said dispenser in service, said applicator tip cover being integrally formed with said compressible reservoir.

2. The dispenser of claim 1, wherein said liquid product is sealed within the confines of said compressible reservoir and said applicator tip to prevent leakage prior to placing said dispenser in service.

3. In combination, a predetermined quantity of liquid product in a dispenser for the substantially uniform topical application of said liquid product either to discrete isolated portions of the surface of an object or to the entire surface of said object, said combination comprising:
   (a) a predetermined quantity of said liquid product;
   (b) a compressible reservoir for housing said liquid product;
   (c) an applicator tip comprised of substantially non-porous material and having a longitudinal axis and an external surface comprising an exposed portion and a non-exposed portion, said exposed and non-exposed portions being located adjacent one another along said longitudinal axis, said non-exposed portion of said applicator tip being secured in fluid communication with said compressible reservoir, said non-exposed portion of said applicator tip also being in fluid communication with said exposed portion of said applicator tip by means of at least one liquid passageway at least partially comprising said applicator tip, said liquid passageway extending from said compressible reservoir to the initial point of exposure of said exposed portion of said applicator tip, whereby liquid product can be transferred from said compressible reservoir to said exposed surface of said applicator tip along said liquid passageway when said reservoir is compressed, said exposed portion of said applicator tip extending beyond said at least one liquid passageway comprising a cylinder having a rounded end, said cylinder and said rounded end exhibiting a substantially non-porous surface which is sufficiently smooth that said liquid product will sheet substantially uniformly onto said smooth surfaced cylinder and rounded end of said applicator tip as soon as said liquid product exits said at least one liquid passageway, whereby said uniformly sheeted liquid product on said exposed portion of said applicator tip can thereafter be transferred either to discrete isolated portions of the surface of an object by contacting said discrete isolated portions with said liquid product coated rounded end portion of said applicator tip or to the entire surface of said object by tangentially stroking said entire surface with the periphery of said liquid product coated cylinder portion of said applicator tip in a direction substantially perpendicular to the axis of said cylinder; and
   (d) an applicator tip cover for totally enclosing the exposed portion of said applicator tip prior to placing said dispenser in service, said applicator tip cover being integrally formed with said compressible reservoir.

4. The combination of claim 3, wherein said liquid product is sealed within the confines of said compressible reservoir and said applicator tip to prevent leakage prior to placing said combination in service.

* * * * *

UNITED STATES PATENT AND TRADEMARK OFFICE
CERTIFICATE OF CORRECTION

PATENT NO. : 5,006,004

DATED : April 9, 1991

INVENTOR(S) : Robert S. Dirksing; Theodore P. Merz

It is certified that error appears in the above-identified patent and that said Letters Patent is hereby corrected as shown below:

TITLE PAGE:
Inventors: "Theodore F. Merz" should read -- Theodore P. Merz -- .

Title page, Assignee: "Proctor" should read -- Procter -- .

In the References Cited Section, Column 2, Patent No. 4,636,203 Emanis et al. "1/1967" should read -- 1/1987 -- .

Column 1, line 19, delete "disclosed" second occurrence.

Column 2, line 28, "maerial" should read -- material -- .

Column 7, line 17, "MINOXIDI" should read -- MINOXIDIL -- .

Column 7, line 50, delete "a" .

Column 8, line 34, "comprises" should read -- comprised -- .

Column 8, line 55, "food" should read -- foot -- .

Signed and Sealed this

Twenty-fifth Day of August, 1992

*Attest:*

DOUGLAS B. COMER

*Attesting Officer*      *Acting Commissioner of Patents and Trademarks*